(12) United States Patent
Yang et al.

(10) Patent No.: US 7,763,285 B2
(45) Date of Patent: Jul. 27, 2010

(54) POLYACETYLENIC COMPOUNDS

(75) Inventors: Wen-Chin Yang, Dah-An Shiang (TW); Lee-Tian Chang, Taichung (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 11/674,105

(22) Filed: Feb. 12, 2007

(65) Prior Publication Data

US 2008/0193568 A1 Aug. 14, 2008

(51) Int. Cl.
  A61K 36/00 (2006.01)
  A61K 31/70 (2006.01)
  C07H 1/00 (2006.01)
(52) U.S. Cl. .......................... 424/725; 514/23; 514/25; 514/35; 514/866; 536/1.11
(58) Field of Classification Search ........................ None
See application file for complete search history.

(56) References Cited

U.S. PATENT DOCUMENTS

2007/0053998 A1  3/2007  Yang et al.

FOREIGN PATENT DOCUMENTS

| JP | 2002205954 | | 7/2002 |
| JP | 2004083463 | | 3/2004 |
| JP | 2004083463 | A * | 3/2004 |
| WO | WO 95/23214 | | 8/1995 |

OTHER PUBLICATIONS

Ubillas et al (Planta Med 66: 82-83, 2000).*
Christiansen et al, discovery of potent and selective agonists for the free fatty acid receptor 1 (FFA1/GPR 40), a potential target for the treatment of type II diabetes, J. Med. Chem 2008, 61: 7061-7064.*
Ren et al, Synthesis and structure-activity relationship study of antidiabetic penta-O-gallyol-D-dlucopyranose and its analogues, J Med Chen 2006,49: 2829-2837.*
Neogi et al, Synthesis and structure-activity relationship studies of cinnamic acid-based novel thiazolidinedione antihyperglycemic agents, Bioorganic & Medicinal Chemistry 11 (2003) 4059-4067.*
Kim et al, Design, synthesis, and structure-activity relationship of carbamate-tethered aryl propanoic acids as novel PPAR alpha/gamma dual agonists, Bioorganic & Medicinal Chemistry Letters 17 (2007) 3595-3598.*
Miura et al, Hypoglycemic activity and structure-activity relationship of iridoidal glycosides, Bio Pharm Bull. 1996, 19 (1): 160-1.*
Chang et al., "Polyacetylenic Compounds and Butanol Fraction from Bidens pilosa can Modulate the Differentiation of Helper T Cells and Prevent Autoimmune Diabetes in Non-Obese Diabetic Mice," Planta Med., 70: 1045-1051 (2004).
Chang et al., "The distinct effectsd of a butanol fraction of Bidens pilosa plant extract on the development of TH1-mediated diabetes and Th2-mediated airway inflammation in mice," Journal of Biomedical Science, 12:79-89 (2005).
Chiang et al., "Cytopiloyne, a novel polyacetylenic glucoside from Bidens pilosa, functions as a T helper cell modulator," Journal of Ethnopharmacology, 110:532-538 (2007).
Ubillas et al., "Antihyperglycemic Acetylenic Glucosides from Bidens pilosa," Planta Med., 66:82-83 (2000).
Wu, et al.; "Polyacetylenes Function as Anti-Angiogenic Agents"; Pharmaceutical Research; vol. 2: 2112-2119 (Nov. 2004).
McClenaghan, et al.; "Physiological and pharmacological regulation of insulin release: insights offered through exploitation of insulin-secreting cell lines"; Diabetes, Obesity and Metabolism; 137-150 (1999).
Vinik, et al.; "Prevention of the Complications of Diabetes"; The American Journal of Managed Care; vol. 9; S63-S80, (2003).
Boyle, et al.; "Estimating Prevalence of Type 1 and Type 2 Diabetes in a Population of African Americans with Diabetes Mellitus"; American Journal of Epidemiology, vol. 149; 55-63; (1999).
Melloul, et al.; "Regulation of insulin gene transcription"; Diabetologia; 45: 309-326; (2002).
Del Prato, et al.; "The importance of first-phase insulin secretion: implications for the therapy of type 2 diabetes mellitus"; Diabetes/Metabolism Research and Reviews; 17: 164-174; (2001).
Attele, et al.; "Antidiabetic Effects of *Panax ginseng* Berry Extract and the Identification of an Effective Component"; Diabetes; vol. 51, 1851-1858; Jun. 2002.
Ravid, et al.; "Cardiovascular protection in patients with type 2 diabetes mellitus: Considerations about the tightness of blood pressure control and the choice of treatment"; European Journal of Internal Medicine; 16: 154-159 (2005).
Bell; "Type 2 Diabetes Mellitus: What is the Optimal Treatment Regimen?"; The American Journal of Medicine; vol. 116: 23S-29S (2004).
Verspohl, E.J.; "Recommended Testing in Diabetes Research"; Planta Med. 68: 581-590; (2002).
Wicksteed, et al.; "Glucose-induced Translational Control of ProinsulinBiosynthesis Is Proportional to Preproinsulin mRNA Levels in Islet B-Cells but Not Regulated via a Positive Feedback of Secreted Insulin*"; The Journal of Biological Chemistry; vol. 278, 43: 42080-42090 (2003).

(Continued)

*Primary Examiner*—Patricia Leith
*Assistant Examiner*—Qiuwen Mi
(74) *Attorney, Agent, or Firm*—Occhiuti Rohlicek & Tsao LLP

(57) ABSTRACT

A method of treating type II diabetes with a polyacetylenic compound of the following formula:

$$R_1 \!-\!\!\!\left(C\!\equiv\!C\right)_{\!m}\!\!\left(\!\!\begin{array}{c}C\!=\!C\\H\ \ H\end{array}\!\!\right)_{\!n}\!\!\left(\ \ \right)_{\!o}\!\!\overset{OR_2}{\underset{}{\diagup}}\!\!\left(\ \ \right)_{\!p}\!\!OR_3,$$

in which $R_1$ is H, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, or heteroaryl; $R_2$ is H or a monosaccharide residue; $R_3$ is H or $C_1$-$C_{10}$alkyl; m is 2, 3, or 4; n is 0, 1, 2, or 3; o is 0, 1, 2, 3, or 4; and p is 1, 2, 3, or 4.

3 Claims, No Drawings

OTHER PUBLICATIONS

Henquin, "Perspectives in Diabetes Triggering and Amplifying Pathways of Regulation of Insulin Secretion by Glucose"; Diabetes, 49: 1751-1760, 2000.

Leibiger, et al.; "Exocytosis of Insulin Promotes Insulin Gene Transcription via the Insulin Receptor/PI-3 Kinase/p70 s6 Kinase and CaM Kinase Pathways"; Molecular Cell; vol. 1: 933-938 (1998).

Oubré, et al.; "From Plant to patient: An ethnomedical approach to the identification of new drugs for the treatment of NIDDM"; Diabetologia; 40: 614-617 (1997).

Habeck, M.; "Diabetes treatments get sweet help from nature"; Nature Medicine; vol. 9: 1228; (2003).

Alarcon-Aguilar, et al.; "Investigation on the Hypoglycaemic Effects of Extracts of Four Mexican Medicinal Plants in Normal and Alloxan-diabetic Mice"; Phytotherapy Research; 16: 383-386 (2002).

Krettli, et al.; "The Search for New Antimalarial Drugs from Plants Used to Treat Fever and Malaria or Plants Ramdomly (sic) Selected: a Review"; *Mem Inst Oswaldo Cruz*; vol. 96(8): 1033-1042 (2001).

Geissberger et al., "Constituents of *Bidens pilosa* L.: Do the components found so far explain the use of this plant in traditional medicine?" Acta Tropica 48:251-261, 1991.

Jager et al., "Screening of Zulu medicinal plants for prostaglandin-synthesis inhibitors" Journal of Ethnopharmacology 52:95-100, 1996.

Rabe et al., "Antibacterial activity of South African plants used for medicinal purposes" Journal of Ethnopharmacology 56:81-87, 1997.

Alvarez et al., "Bioactive Polyacetylenes from *Bidens pilosa*" Planta Medica 62:355-357, 1996.

Abbas et al., "T Lymphocytes and the Initiation of Cell-Mediated Immune Reactions" Cellular and Molecular Immunology, Section III 262-277, 1997.

Abbas et al., "Functional diversity of helper T lymphocytes" Nature 383:787-793, Oct. 31, 1996.

Farnsworth, "The Role of Medicinal Plants in Drug Development" Natural Products and Drug Development, Alfred Benzon Symposium 20, 1984.

Pereira et al., "Immunosuppressive and anti-inflammatory effects of methanolic extract and polyacetylene isolated from *Bidens pilosa* L." Immunopharmacology 43:31-37, 1999.

Brandao et al., "Antimalarial activity of extracts and fractions from *Bidens pilosa* and other *Bidens* species (Asteraceae) correlated with the presence of acetylene and flavonoid compounds" Journal of Ethnopharmacology 57:131-138, 1997.

Chih et al., "Anti-inflammatory Activity of Taiwan Folk Medicine "Ham-Hong-Chho" in Rats" American Journal of Chinese Medicine, vol. XXIII, Nos. 3-4, pp. 273-278, 1995.

Rucker et al., "Acetylenic Glucosides from *Microglossa pyrifolia*" Planta Medica 58:266-269, 1992.

Ubillas et al., "Antihyperglycemic Acetylenic Glucosides from *Bidens pilosa*" Planta Medica 66:82-83, 2000.

Chang, et al., "Polyacetylenic Compounds and Butanol Fraction from *Bidens pilosa* can Modulate the Differentiation of Helper T Cells and Prevent Autoimmune Diabetes in Non-Obese Diabetic Mice"; Planta Medica, 70(11): 1045-1051, 2004.

Zhao, et al., "A New Chalcone Glycoside from *Bidens pilosa*", Acta Botanica Yunnanica, 2004, 26 (1): 121-126.

* cited by examiner

POLYACETYLENIC COMPOUNDS

BACKGROUND

Type II diabetes is a disease marked by hyperglycemia, i.e., high levels of glucose in the blood. Many patients of type II diabetes suffer various life-threatening complications resulting from long-term hyperglycemia. Effective control of blood glucose levels is the key to preventing or reversing diabetic complications.

Insulin secretion plays an important role in regulating blood glucose levels. Therefore, there is a need to identify compounds that enhance insulin secretion, thereby effectively treating type II diabetes.

SUMMARY

This invention is based on the unexpected finding that a naturally occurring polyacetylenic compound was effective in treating type II diabetes.

In one aspect, this invention features a pure compound of formula (I):

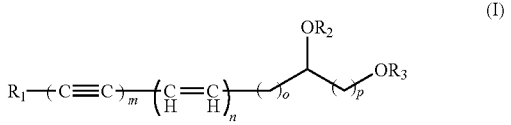

In this formula, $R_1$ is H, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, or heteroaryl; $R_2$ is a monosaccharide residue; $R_3$ is H or $C_1$-$C_{10}$ alkyl; m is 2, 3, or 4; n is 0, 1, 2, or 3; o is 0, 1, 2, 3, or 4; and p is 1, 2, 3, or 4. The term "pure compound" refers to a compound that has a purity of at least 80% (e.g., 95% or 99%). Referring to formula (I), a subset of the polyacetylenic compounds described above are those in which $R_1$ is $C_1$-$C_{10}$ alkyl (e.g., methyl), $R_2$ is glycopyranose; $R_3$ is H or $C_1$-$C_{10}$ alkyl; m is 4; n is 0; o is 2; and p is 1.

The term "alkyl" refers to a saturated, linear or branched, non-aromatic hydrocarbon moiety, such as $CH_3$, $-CH_2-$, or branched $(CH_3)_2CH_2-$. The term "alkenyl" refers to a linear or branched, non-aromatic hydrocarbon moiety having at least one double bond, such as $CH_2=CH-$, or $-CH=CH-$. The term "alkynyl" refers to a linear or branched, non-aromatic hydrocarbon moiety having a least one triple bond, such as $CH\equiv C-$ or $-C\equiv C-$. The term "cycloalkyl" refers to a saturated non-aromatic cyclic hydrocarbon moiety, such as cyclohexyl. The term "cycloalkenyl" refers to a non-aromatic, cyclic hydrocarbon moiety that contains at least one double bond in the ring, such as cyclohexenyl. The term "heterocycloalkyl" refers to a saturated non-aromatic, cyclic moiety having at least one ring heteroatom (e.g., O, N, or S), such as 4-tetrahydropyranyl. The term "heterocycloalkenyl" refers to a non-aromatic, cyclic moiety having at least one ring heteroatom and at least one double bond in the ring, such as pyranyl. The term "aryl" refers to a hydrocarbon moiety having at least one aromatic ring. Examples of aryl moieties include phenyl, phenylene, biphenyl, naphthyl, naphthylene, pyrenyl, anthryl, and phenanthryl. The term "heteroaryl" refers to a moiety having at least one aromatic ring which contains at least one heteroatom. Examples of heteroaryl moieties include furyl, furylene, fluorenyl, pyrrolyl, thienyl, oxazolyl, imidazolyl, thiazolyl, pyridyl, pyrimidinyl, quinazolinyl, isoquinolyl, and indolyl.

Alkyl, alkenyl, alkynyl, cycloalkyl, cycloalkenyl, heterocycloalkyl, heterocycloalkenyl, aryl, and heteroaryl mentioned herein include both substituted and unsubstituted moieties. Examples of substituents on cycloalkyl, cycloalkenyl, heterocycloalkyl, heterocycloalkenyl, aryl, and heteroaryl include, but are not limited to, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{10}$ alkoxy, aryl, aryloxy, heteroaryl, heteroaryloxy, amino, $C_1$-$C_{10}$ alkylamino, $C_1$-$C_{20}$ dialkylamino, arylamino, diarylamino, heteroarylamino, diheteroarylamino, $C_1$-$C_{10}$ alkylsulfony, arylsulfonyl, heteroarylsulfonyl, $C_1$-$C_{10}$ alkylsulfonamide, arylsulfonamide, heteroarylsulfonamide $C_1$-$C_{10}$ alkylimino, arylimino, $C_1$-$C_{10}$ alkylsulfonimino, alrylsulfonimino, hydroxyl, halo, thio, $C_1$-$C_{10}$ alkylthio, arylthio, aminothioacyl, amidino, guanidine, ureido, cyano, nitro, nitroso, azido, acyl, thioacyl, acyloxy, carboxyl, amido, carbamoyl, and carboxyl, and carboxylic ester. Examples of substituents on alkyl, alkenyl, and alkynyl include all of the above-recited substituents except $C_1$-$C_{10}$ alkyl, $C_2$-$C_{10}$ alkenyl, and $C_2$-$C_{10}$ alkynyl. Cycloalkyl, cycloalkenyl, heterocycloalkyl, heterocycloalkenyl, aryl, and heteroaryl can also be fused with each other.

In another aspect, this invention features a method for treating type II diabetes by administering to a subject in need an effective amount of a polyacetylenic compound of formula (I) shown above, in which $R_1$ is H, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, or heteroaryl; $R_2$ is H or a monosaccharide residue; $R_3$ is H or $C_1$-$C_{10}$ alkyl; m is 2, 3, or 4; n is 0, 1, 2, or 3; o is 0, 1, 2, 3, or 4; and p is 1, 2, 3, or 4. A subset of the polyacetylenic compounds are those in which $R_1$ is $C_1$-$C_{10}$ alkyl (e.g., methyl); $R_2$ is a glucose, galactose, fucose, mannose, gulose residue, or H; $R_3$ is H; m is 4, n is 0, o is 2, and p is 1. A polyacetylenic compound can be administered to the subject as a pure compound in a pharmaceutical composition or as a component in a *Bidens pilosa* extract (see below).

In a further aspect, this invention features a method for treating type II diabetes by administering to a subject in need an effective amount of a *Bidens pilosa* preparation. Such a preparation can be obtained by stirring pulverized *Bidens pilosa* plants in water at an elevated temperature (e.g., at 50° C. or 100° C.) to form a suspension, and collecting a supernatant of the suspension. The supernatant can be further extracted with an alcohol (e.g., n-butanol) to provide an enriched preparation. The *Bidens pilosa* preparation contains one or more of the polyacetylenic compounds of the just-mentioned formula (I). For example, it contains cytopiloyne:

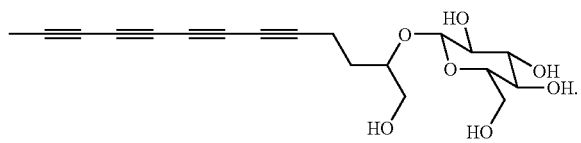

The polyacetylenic compounds described above include the compounds themselves, as well as their salts, prodrugs, and solvates, if applicable. Such salts, for example, can be formed by interaction between a negatively charged substituent (e.g., carboxylate) on a polyacetylenic compound and a cation. Suitable cations include, but are not limited to, sodium ion, potassium ion, magnesium ion, calcium ion, and an ammonium cation (e.g., tetramethylammonium ion). Likewise, a positively charged substituent (e.g., amino) on a polyacetylenic compound can form a salt with a negatively charged counterion. Suitable counterions include, but are not limited to, chloride, bromide, iodide, sulfate, nitrate, phosphate, or acetate. Examples of prodrugs include esters and other pharmaceutically acceptable derivatives, which, upon administration to a subject, are capable of providing above compounds described above. A solvate refers to a complex formed between a polyacetylenic compound and a pharmaceutically acceptable solvent. Examples of pharmaceutically acceptable solvents include water, ethanol, isopropanol, n-butanol, ethyl acetate, and acetic acid.

The polyacetylenic compounds may contain one or more asymmetric centers or a non-aromatic double bond. Thus, they can occur as racemates and racemic mixtures, single enantiomers, individual diastereomers, diastereomeric mixtures, and cis- and trans-isomeric forms. All such isomeric forms are contemplated.

Also within the scope of this invention is a composition, including a *Bidens pilosa* extract, containing one or more of the polyacetylenic compounds described above for use in treating type II diabetes, and the use of such a composition for the manufacture of a medicament for the just-mentioned treatment.

The details of the embodiments of the invention are set forth in the description below. Other features, objects, and advantages of the invention will be apparent from the following description and from the claims.

DETAILED DESCRIPTION

This invention relates to using polyacetylenic compounds for treating type II diabetes.

Some of the polyacetylenic compounds (e.g., cytopiloyne) can be isolated from *Bidens pilosa* as follows. Whole *Bidens pilosa* plants are first pulverized and then stirred in heated water. After removal of insoluble materials (e.g., by filtration, decantation, or centrifugation), the resultant supernatant is subjected to liquid chromatography (e.g., high-pressure liquid chromatography) or other suitable methods to afford pure polyacetylenic compounds. The pure compounds thus obtained can be further derivatized to provide a number of other polyacetylenic compounds of this invention.

The polyacetylenic compounds described above can also be prepared by conventional methods. Below are three reaction schemes illustrating synthetic routes to a polyacetylenic compound of this invention.

Butane-1,2,4-triol (i) is reacted with acetone to form a protected 1,2,4-triol compound (ii), which can be readily transformed to a iodo derivative (iii). Compound (iii) is then reacted with ethynyltrimethylsilane, under a basic condition (e.g., n-BuLi), to give (4-(2,2-dimethyl-1,3-dioxolan-4-yl)but-1-ynyl)trimethylsilane (iv). Compound (iv) is subsequently treated with an acid (e.g., acetic acid), followed by a coupling reaction with 2-bromoglucopyranose to afford an adduct (v). Compound (v) can be further treated with potassium fluoride to afford 2-phenyl-4H-chromen-4-one (vi).

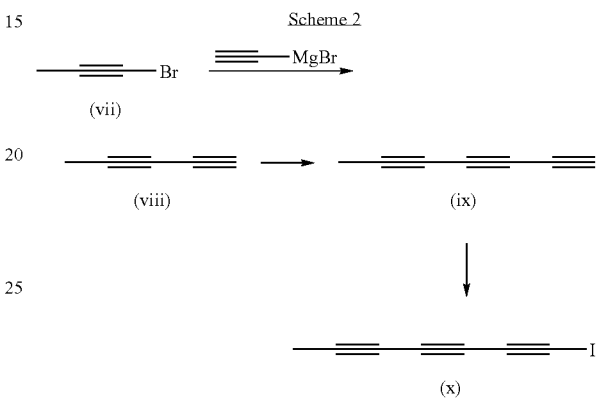

1-Bromoprop-1-yne (vii) is reacted with ethynylmagnesium bromide to afford penta-1,3-diyne (viii), which is further converted to hepta-1,3,5-triyne (ix). Compound (ix) can be readily transformed to 1-iodohepta-1,3,5-triyne (x) under a basic condition (e.g., n-BuLi), followed by addition of an iodo compound (e.g., $I_2$).

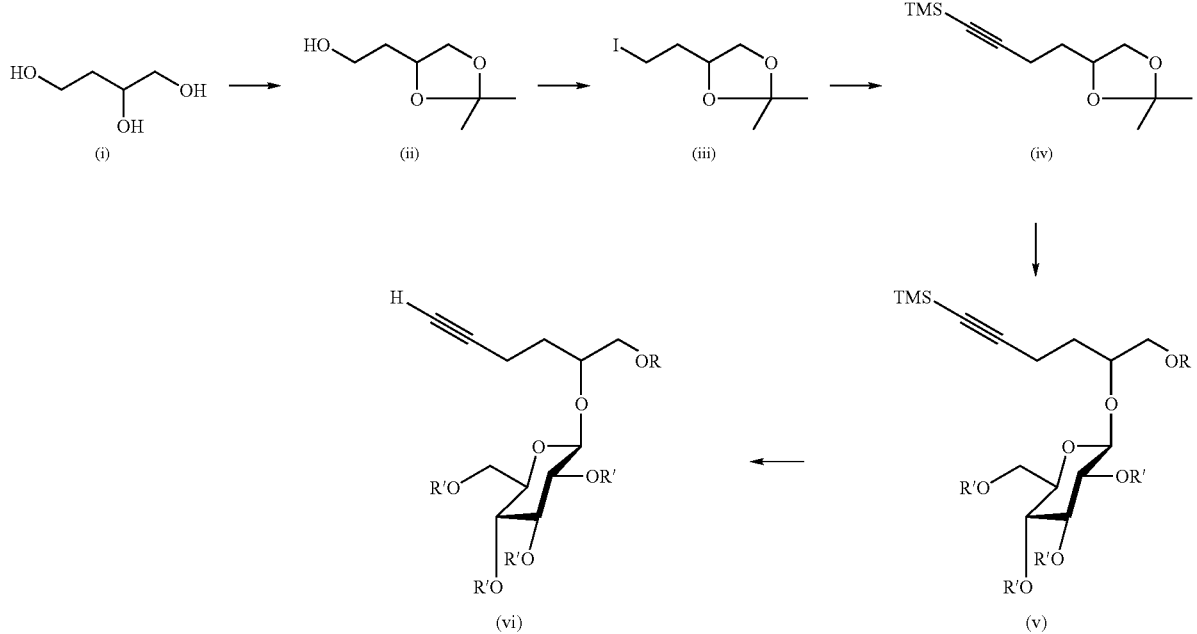

Scheme 3

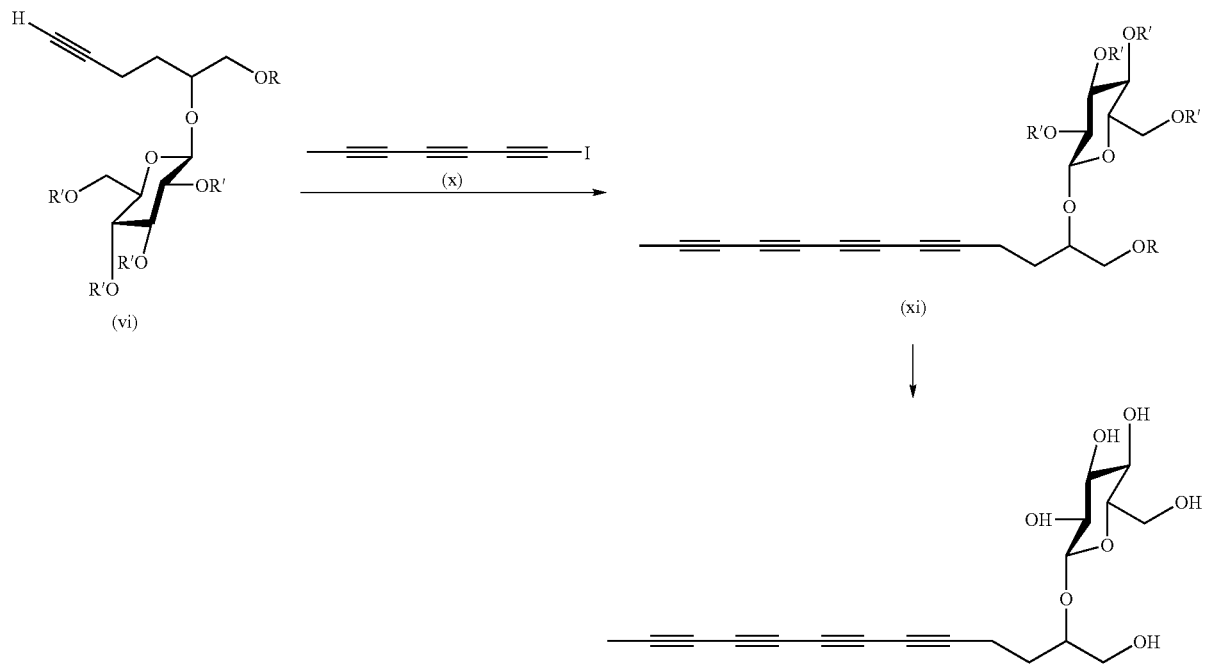

Scheme 3 demonstrates a coupling reaction between an acetylene derivative (vi), obtained from Scheme 1, and 1-iodohepta-1,3,5-triyne (x), obtained from Scheme 2, to a tetrayne compound (xi). Removal of protecting groups affords a polyacetylenic compound, 2β-D-glucopyranosyloxy-1-hydroxytrideca-5,7,9,11-tetrayne, a compound of this invention.

Synthetic chemistry transformations useful in synthesizing applicable compounds are described, for example, in R. Larock, *Comprehensive Organic Transformations*, VCH Publishers (1989); T. W. Greene and P. G. M. Wuts, *Protective Groups in Organic Synthesis*, 3$^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

This invention features a method of administrating an effective amount of one of the above-described polyacetylenic compounds or a *Bidens pilosa* preparation containing such a compound to a subject for treating type II diabetes. The term "treating" refers to administration of an effective amount of the compound of formula (I) to a subject, who has type II diabetes, or a symptom or predisposition toward such a disease, with the purpose to cure, alleviate, relieve, remedy, ameliorate, or prevent type II diabetes, the symptoms of it, or the predispositions towards its. Such a subject can be identified by a health care professional based on results from any suitable diagnostic method. "An effective amount" refers to the amount of an active thiophene compound that is required to confer a therapeutic effect on the treated subject. Effective doses will vary, as recognized by those skilled in the art, depending on route of administration, excipient usage, and the possibility of co-usage with other therapeutic treatment.

When treating type II diabetes with a polyacetylenic compound (either as a pure compound or in a *Bidens pilosa* extract), they can be administered parenterally, orally, nasally, rectally, topically, or buccally. The term "parenteral" as used herein refers to subcutaneous, intracutaneous, intravenous, intramuscular, intraarticular, intraarterial, intrasynovial, intrasternal, intrathecal, intralesional, or intracranial injection, as well as any suitable infusion technique.

A sterile injectable composition can be a solution or suspension in a non-toxic parenterally acceptable diluent or solvent, such as a solution in 1,3-butanediol. Among the acceptable vehicles and solvents that can be employed are mannitol, water, Ringer's solution, and isotonic sodium chloride solution. In addition, fixed oils are conventionally employed as a solvent or suspending medium (e.g., synthetic mono- or diglycerides). Fatty acid, such as oleic acid and its glyceride derivatives are useful in the preparation of injectables, as are natural pharmaceutically acceptable oils, such as olive oil or castor oil, especially in their polyoxyethylated versions. These oil solutions or suspensions can also contain a long chain alcohol diluent or dispersant, or carboxymethyl cellulose or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions, and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art. A composition having one or more active above-described compounds can also be administered in the form of suppositories for rectal administration.

A pharmaceutically acceptable carrier is routinely used with one or more active above-mentioned compounds. The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an above-mentioned compound. Examples of other carriers include colloidal silicon oxide, magnesium stearate, cellulose, sodium lauryl sulfate, and D&C Yellow #10.

The polyacetylenic compounds described above lower blood glucose levels by enhancing insulin synthesis and insulin secretion. They can be preliminarily screened for their efficacy in treating type II diabetes by in vitro assays or by animal experiments, and then confirmed by clinic trials. Other methods will also be apparent to those of ordinary skill in the art.

The specific examples below are to be construed as merely illustrative, and not limitative of the remainder of the disclosure in any way whatsoever. Without further elaboration, it is believed that one skilled in the art can, based on the description herein, utilize the present invention to its fullest extent.

EXAMPLE 1

*Bidens pilosa* plants were collected from the campus of Academia Sinica, Taiwan. Approximately 10 kg of cleaned and crushed plants, in their entirety, was refluxed in 40 L of water for two hours. After removal of aqueous phase, insoluble materials was again refluxed in 25 L of water for two hours. The combined aqueous solutions (approximately 65 L) were evaporated in vacuo to yield a residue, which was subsequently suspended in 1.0 L of water and extracted with 1.0 L of n-butanol for three times. The n-butanol fraction was first evaporated on a vacuum rotary evaporator under reduced pressure and then lyophilized to provide a crude product of cytopiloyne (37.7 g).

The crude product was subsequently chromatographed over a RP-18 silica gel column with a $CH_3OH/H_2O$ gradient solvent system to give sub-fractions BPB1, BPB2, BPB3, and BPB4. The BPB3 fraction, eluted by 70% $CH_3OH$, was further fractionated by semi-preparative HPLC using a $CH_3OH/H_2O$ solvent system. Cytopiloyne was obtained and characterized by $^1H$ NMR and $^{13}C$ NMR.

$^1H$ NMR (500 MHz, $CDOD_3$) δ 1.78 (2H, q, J=6.8 Hz), 1.98 (3H, s), 2.58 (2H, t, J=6.8 Hz), 3.19 (1H, dd, J=9.1, 7.8 Hz), 3.30 (1H, m), 3.34 (1H, m), 3.59 (2H, m), 3.65 (1H, dd, J=12.0, 6.5 Hz), 3.75 (1H, p, J=6.8 Hz), 3.85 (1H, dd, J=12.0, 1.7 Hz), 4.32 (1H, d, J=7.8 Hz); $^{13}C$ NMR (125 MHz, $CDOD_3$) δ 3.8, 16.1, 31.4, 60.0, 60.9, 61.8, 62.4, 62.6, 64.9, 65.8, 66.2, 71.5, 75.2, 77.9, 81.6, 104.8.

EXAMPLE 2

The db/db mice were purchased from Jackson Laboratory (Bar Harbor, Me., U.S.A.), and then maintained and handled according to the guidelines of Academia Sinica Institutional Animal Care and Utilization Committee (Taiwan).

Diabetic db/db mice of 7-8 weeks old were fasted for 12 hours (water allowed), and then intraperitoneally injected with phosphate-buffered saline (PBS) or cytopiloyne at 25 µg/kg, blood glucose levels in the mice were monitored at 0, 1, 2, 4, and 6 hours using Elite glucometer.

The results show that at two hours the blood glucose levels in treated mice significantly decreased.

EXAMPLE 3

The db/db mice were purchased from Jackson Laboratory, and then maintained and handled according to the guidelines of Academia Sinica Institutional Animal Care and Utilization Committee (Taiwan). Glibenclamide was purchased from MP Biomedical Inc.

Diabetic db/db mice aged 7-8 weeks were fasted for 12 hours (water allowed) and orally administered with PBS, cytopiloyne at 0.5 mg/kg or Glimepiride at 2.5 mg/kg. Half an hour later, the mice were intraperitoneally injected with glucose at 0.5 g/kg body weight. Blood glucose levels were monitored at 0, 0.5, 1, 1.5, 2 and 3 hours using Elite glucometer.

The results show that cytopiloyne at 0.5 mg/kg body weight improved glucose tolerance as effectively as Glimepiride at 2.5 mg/kg body weight, as opposed to PBS in mice.

EXAMPLE 4

RIN-m5F cells, at rat β cell line, were obtained from the American Type Culture Collection (ATCC). Glucose-free RPMI medium was purchased from Life Technology. The cells were grown in a glucose-free RPMI 1640 medium supplemented with 10% FCS, penicillin (100 U/ml), streptomycin (100 µg/ml), 2-mercapoethanol (50 µM), sodium pyruvate (1 mM), and glutamate (292 µg/ml).

The cells were separately incubated with vehicle, glucose at a high dose (16.7 mM), glucose at a low dose (3.6 mM), and cytopiloyne at 2.5, 10, and 15 µg/mL for 24 hours. Insulin levels in the cell medium were determined using an insulin Elisa kit (Mercodia, Uppsala, Sweden).

The results show that cytopiloyne significantly enhanced insulin secretion.

EXAMPLE 5

RIN-m5F cells were pre-treated with vehicle, diazoxide (100 µM), EGTA (10 µM), or nimodipine (1 µM) for 30 minutes. They were then incubated wit cytopiloyne at 5 µg/ml for 10 min. Insulin levels in the cell medium were determined using an insulin Elisa kit.

It was observed that diazoxide, a potassium/ATP channel opener, suppressed cytopiloyne-induced insulin secretion. EGTA, a calcium chelator, and nimodipine, a calcium channel blocker, suppressed cytopiloyne-mediated insulin secretion in β cells.

These results suggest that cytopiloyne induced insulin secretion by affecting the functions of potassium/ATP channel and calcium channel.

EXAMPLE 6

The pINS-DCR3 vector containing a human insulin promoter was digested by SphI and BamHI and then cloned into a pcDNAΔCMVlue vector to generate the plasmid pINS-Luc. The plasmid pRL-TK containing a thymidine kinase promoter and a *Renilla* luciferase reporter gene was purchased from Promega.

RIN-m5F cells transfected with pINS-Luc and pRL-TK plasmids were incubated with vehicle, high glucose (16.7 mM), or cytopiloyne at 2.5, 10, or 15 μg/ml for 24 hours.

The results show that cytopiloyne stimulated insulin transcription in RIN-m5F cells in a dose-dependent manner.

EXAMPLE 7

Primary β cells from mice were seeded in 9-cm² placates in a glucose-free RPMI 1640 medium. Both mouse primary β cells and RIN-m5F cells were treated with vehicle or cytopiloyne at 2.5, 5, or 10 μg/ml for 24 hours. The treated cells were subsequently subjected to intracellular staining with anti-insulin antibody (H86, Santa Cruz Biotechnology, CA, USA) and FITC-conjugated anti-rabbit antiserum (BD Biosciences, CA, USA) according to the manufacturer's instruction. The insulin levels in the cell media were determined using an insulin Elisa kit.

The results show that cytopiloyne elevated insulin levels in β cells in comparison with vehicle treatment.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

Furthermore, from the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method of treating type II diabetes, comprising administering to a subject in need thereof an effective amount of pure cytopiloyne, having a chemical structure of

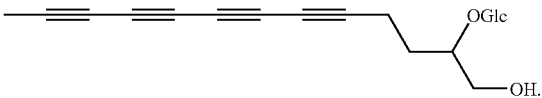

2. The method of claim 1, wherein the pure cytopiloyne is synthesized.

3. The method of claim 1, wherein the pure cytopiloyne is isolated from *Bidens pilosa.*

* * * * *